(12) United States Patent
Takimoto et al.

(10) Patent No.: US 9,551,652 B2
(45) Date of Patent: Jan. 24, 2017

(54) CHLORINE DIOXIDE GAS CONCENTRATION MEASURING APPARATUS

(71) Applicants: TAKIMOTOGIKEN KOGYO CO., LTD., Nagoya (JP); C.S.D CO., LTD., Nagoya (JP)

(72) Inventors: Masateru Takimoto, Nagoya (JP); Katsuji Hotta, Nagoya (JP)

(73) Assignees: TAKIMOTOGIKEN KOGYO CO., LTD., Nagoya (JP); C.S.D. CO., LTD., Nagoya (JP)

( * ) Notice: Subject to any disclaimer, the term of this patent is extended or adjusted under 35 U.S.C. 154(b) by 0 days.

(21) Appl. No.: 14/950,029

(22) Filed: Nov. 24, 2015

(65) Prior Publication Data

US 2016/0153897 A1 Jun. 2, 2016

(30) Foreign Application Priority Data

Nov. 25, 2014 (JP) ................................. 2014-237529

(51) Int. Cl.
*G01N 21/33* (2006.01)
*G01N 21/61* (2006.01)
(Continued)

(52) U.S. Cl.
CPC .............. *G01N 21/33* (2013.01); *G01N 21/61* (2013.01); *G01N 21/85* (2013.01);
(Continued)

(58) Field of Classification Search
None
See application file for complete search history.

(56) References Cited

U.S. PATENT DOCUMENTS 5,896,088 A * 4/1999 Brooks, Jr. ........ G01N 21/3504
250/338.5

FOREIGN PATENT DOCUMENTS

| JP | 1979-10784 | 1/1979 |
| JP | 1985-041849 | 3/1985 |

(Continued)

OTHER PUBLICATIONS

Ayako Yokoi, Japanese Office Action Dispatch No. 673962 for JP Application No. 2014-23759, Jan. 6, 2015.
(Continued)

*Primary Examiner* — Kara E Geisel
*Assistant Examiner* — Amanda Merlino
(74) *Attorney, Agent, or Firm* — Trego, Hines & Ladenheim, PLLC

(57) ABSTRACT

A measuring apparatus is capable of measuring chlorine dioxide gas concentration by correcting for changes in light emission of an LED due to heating and passage of time, and applying the correction to the optical absorption rate of chlorine dioxide gas at a photodetector. The measuring apparatus includes a main body with a measuring passage surrounded by a pair of transparent bodies, into which specimen gas or fresh air is fed and then discharged, and a comparing passage arranged in the vicinity of the measuring passage, into which no specimen gas is fed, first and second LEDs for emitting ultraviolet light which both have identical properties and are mounted at one end of the measuring passage and at one end of the comparing passage, respectively, and first and second photodetectors for receiving light respectively from the first and second LEDs and detecting a light emission amount thereof.

4 Claims, 7 Drawing Sheets

(51) Int. Cl.
*G01N 21/85* (2006.01)
*G01N 33/00* (2006.01)
*G01N 21/15* (2006.01)

(52) U.S. Cl.
CPC ... *G01N 33/0036* (2013.01); *G01N 2021/151* (2013.01); *G01N 2021/158* (2013.01); *G01N 2021/8578* (2013.01); *G01N 2201/023* (2013.01)

(56) References Cited

FOREIGN PATENT DOCUMENTS

| | | | |
|---|---|---|---|
| JP | 1986-138528 | 12/1987 | |
| JP | 1995-503791 | 4/1995 | |
| JP | 1995-044829 | 11/1995 | |
| JP | 1998-311790 | 5/2000 | |
| JP | 2000-180360 | 6/2000 | |
| JP | 2008-070364 | 3/2008 | |
| JP | 2009-168478 | 7/2009 | |
| JP | 2009-276281 | 11/2009 | |
| JP | 5639294 | 10/2014 | |
| WO | WO 2010006042 A1 * | 1/2010 | ............. G01N 21/33 |

OTHER PUBLICATIONS

Ayako Yokoi, Japanese Office Action Dispatch No. 166538 for JP Application No. 2014-23759, Apr. 7, 2015.

* cited by examiner

CHLORINE DIOXIDE GAS CONCENTRATION MEASURING APPARATUS

BACKGROUND OF THE INVENTION

Field of the Invention

The present invention generally relates to apparatuses for measuring the concentration of chlorine dioxide gas in an enclosed space, and particularly relates to a chlorine dioxide gas concentration measuring apparatus which uses ultraviolet light.

Description of the Related Art

Chlorine dioxide gas is effective in performing disinfection or fumigation in an enclosed space, and is most effective in performing disinfection in factories that produce food or medicine, for example, and which require that a hygienic environment be maintained. The applicant has made various proposals concerning chlorine dioxide gas generating apparatuses capable of generating such chlorine dioxide gas directly inside factories etc.

Since improper handling of chlorine dioxide gas can cause hazards such as explosions, it is of the utmost importance to ensure that it is possible to adjust and manage the gas concentration in the gas generating apparatus and after generating the gas, depending on the usage conditions. To that end there has been proposed, for example in Japanese Unexamined Patent Application Publication No. 1979-10784, an apparatus for measuring chlorine dioxide gas concentration as a "bleaching compound" in the pulp and paper industry.

Measuring and managing the concentration of chlorine dioxide gas is also important when performing disinfection, and the concentration of gas needs to be measured and managed both during disinfection, and for confirming safety afterwards. In addition, measuring and management of chlorine dioxide gas concentration must be performed in real-time, in order to prevent the occurrence of any unforeseen consequences (such as the aforementioned explosive hazard or adverse effects on personnel) during disinfection.

As discussed in Japanese Unexamined Patent Application Publication No. 1998-311790, chlorine dioxide gas is very toxic, corrosive, and can strongly irritate mucous membranes and the eyes, and has a very low TLV-STEL (threshold limit value-short time exposure) of 0.3 ppm ($ml/m^3$), as defined by the ACGIH (American Conference of Governmental Industrial Hygienists) in 1993 to 1994. It is therefore important to measure the concentration of chlorine dioxide gas in order to avoid the aforementioned adverse effects, and to comply with the threshold limit value of the work environment. Japanese Unexamined Patent Application Publication No. 1998-311790 proposes a chlorine dioxide gas measuring apparatus for this purpose.

The contents of Japanese Unexamined Patent Application Publication No. 1979-10784 and Japanese Unexamined Patent Application Publication No. 1998-311790 are incorporated herein by reference in their entirety.

SUMMARY OF THE INVENTION

Problem to be Solved by the Invention

The "liquid and gas chlorine dioxide photometer" proposed in JP1979-10784 employs the following method, as shown in FIG. 6: "A method of measuring the relative quantity of liquid chlorine dioxide in a flow stream comprising the steps of:
(a) conducting said flow stream between transparent window means;
(b) directing a light beam comprising wavelengths of approximately 4000 to 5000 Angstrom units through said window means and flow stream into photodetector means;
(c) filtering said light beam to permit the exclusive reception of said approximately 4000 to 5000 Angstrom unit light by said photodetector means; and
(d) correlating an electrical characteristic generated by said photodetector means to the relative quantity of chlorine dioxide in said flow stream."

The "4000 to 5000 Angstrom units" are calculated as "400 to 500 nm (nanometers)".

Meanwhile, the "equipment for measuring concentration of chlorine dioxide" described in JP1998-311790 was made with the purpose of "providing equipment and a method for measuring concentration of chlorine dioxide capable of continuously measuring chlorine dioxide concentration that may vary, and of monitoring in real-time the concentration of chlorine dioxide at a manufacturing site or a site being disinfected", (paragraph [0006]) and as indicated in FIG. 7 and the Abstract, the measuring equipment comprises "a flow cell section 20, a supply section for supplying a specimen to the flow cell section 20, a light source section 21 for irradiating the flow cell section 20, and a photometric section 22 for converting the transmitted light into an electrical signal. Between the flow cell section 20 and the photometric section 22 there is provided a wavelength selecting section 23 which makes the transmitted light monochromatic".

JP1998-311790 discloses the following points in detail:

The preferable concentration of chlorine dioxide at a site being disinfected is 0.05 to 300 $ml/m^3$ (=ppm) (paragraph [0012]).

The flow cell ("window means" in JP1979-10784) needs only have transparency and corrosion resistance, and may be made of publically known materials such as glass or quartz (paragraph [0013]).

A mercury discharge lamp and a tungsten lamp can preferably be used as the light source (paragraph [0018]).

It is widely acknowledged that the optical absorption exhibited by chlorine dioxide gas is between around 270 nm to around 500 nm, with an absorption maximum of about 360 nm, and when measuring chlorine dioxide concentration, it is preferable to select a wavelength band that is relatively unaffected when there is a small amount of organic matter present in gas form (paragraph [0018]).

Optimum sensitivity can be obtained by setting the wavelength of the incident light to 365 nm and utilizing excitation light from a mercury discharge lamp capable of supplying light of this wavelength, which was found to eliminate the need for wavelength selection equipment such as interference filters, improving economic efficiency (paragraph [0018]).

The inventors found that a general and most inexpensive method corresponding to this wavelength uses a light emitting diode (LED) as a light source, or through the concomitant use of a tungsten lamp and an interference filter, whereby a sufficient measurement accuracy can be obtained (paragraph [0019]).

The invention can be suitably applied to monitor the concentration of chlorine dioxide gas in the environmental disinfection of bio-clean rooms, such as fumigation of food imports, food processing and medicine manufacture, to sound an alarm, and to determine whether or not it is safe for personnel to enter the room after removal of the chlorine dioxide gas (paragraph [0023]).

In order to make use of the technical information obtained from JP1979-10784 and JP1998-311790, the inventors of the present invention conducted a measuring experiment of chlorine dioxide gas concentration during environmental disinfection using chlorine dioxide gas in a bio-clean room, such as a food processing plant or medicine manufacturing plant, using a commercially available detector with an LED as the light source. After a set period of time had passed, they observed the following problems:

The proper chlorine dioxide gas concentration cannot be measured.

An unexpectedly high concentration is detected.

A condition occurs wherein detection is impossible.

Continuous real-time detection of concentration was not possible.

Upon repeated experimentation and consideration to learn the cause of these problems, the inventors discovered that it involves the following material properties and phenomena.
(1) Although LEDs generate little heat, roughly 30% of the electricity is used up by heat generation.
(2) The light-emitting properties of LEDs change as the LED is heated or deteriorates over time, which affects the actual optical absorption amount of the chlorine dioxide gas.
(3) Between the LED and the photodetector there is arranged a glass window ("window means" in JP1979-10784, "flow cell" in JP1998-311790) that is transparent and has corrosion resistance, to form a containment space for a specimen. When the sample gas supplied between these glass windows contains moisture, this moisture will condense on the glass windows. In general, chlorine dioxide gas is produced as an aqueous solution, and is separated from this solution when used as a gas for fumigation. The chlorine dioxide gas separated from the solution will inevitably contain a lot of water which causes condensation.
(4) Condensation on the inner surfaces of the glass windows will obviously alter the light transmittance between the glass windows, which in turn affects the actual optical absorption amount of the chlorine dioxide gas.
(5) In actual fumigation disinfection using chlorine dioxide gas, with existing LEDs and photodetectors having an error range of 2% to 3%, concentration of the gas must be controlled under very strict conditions; concentration levels must be kept low at 300 ppm, and the process takes about 5 to 6 hours.

The inventors then contemplated how to avoid and correct the aforementioned issues (1) to (5) in order to enable real-time continuous measuring of chlorine dioxide gas concentration, and conceived of the present invention.

It is thus a first object of the present invention to provide a chlorine dioxide gas concentration measuring apparatus that is capable of continuously and precisely measuring chlorine dioxide gas concentration by making a correction for a change in light emission rate of the LED due to heating and passage of time, and constantly applying the correction to the optical absorption rate of the chlorine dioxide gas at the photodetector.

It is also a second object of the present invention to provide a chlorine dioxide gas concentration measuring apparatus that is capable of continuously and precisely measuring chlorine dioxide gas concentration and prevent condensation even if the sample gas contains moisture.

Means for Solving the Problem

In order to solve the aforementioned problem, the invention according to claim 1 employs the following means, described below using the reference numerals of the best mode for carrying out the invention described later:

"A concentration measuring apparatus 100 for measuring a concentration of chlorine dioxide gas in a sample gas selectively fed into the apparatus from a plurality of locations in an enclosed space R via a conduit 50, by means of a change in an amount of ultraviolet light from a LED, using the sample gas which is separately sucked through a plurality of sample gas suction tubes in the enclosed space R and fresh air which is sucked from outside the enclosed space R, the apparatus comprising:

a main body 10 having a measuring passage 11 surrounded by a pair of transparent bodies 13 that transmit light and into which the sample gas or the fresh air is fed respectively from inside or outside of the enclosed space R and then discharged, and a comparing passage 12 arranged in the vicinity of the measuring passage 11 and into which only fresh air is fed from outside the enclosed space R;

a first LED 21 and a second LED 22 for emitting ultraviolet light which both have identical properties and are mounted at one end of the measuring passage 11 and at one end of the comparing passage 12, respectively;

a first photodetector 31 and a second photodetector 32 for receiving light respectively from the first LED 21 and the second LED 22 and detecting a light emission amount thereof;

a plurality of selection valves 52 for individual selection of the sample gas suction tubes;

an inspection valve 53a for controlling feeding of the sample gas from the suction tubes into the main body 10;

an air valve 53b configured to open to enable suction of fresh air from outside the enclosed space R when all of the selection valves 52 are closed; and a pump 51 for enabling suction of the sample gas or fresh air into the main body 10 when either the air valve 53b or any of the selection valves 52 are open, wherein when selectively sucking sample gas from inside the enclosed space R due to the suction of the pump 51 and the selective action of the selection valves 52 over a predetermined time, the inspection valve 53a and the selection valve 52 are temporarily closed and the air valve 53b is opened, so that fresh air is sucked into the main body 10 to discharge all of the sample gas that has been examined, after which the air valve 53b is closed and the inspection valve 53a and another selection valve are opened so that sample gas can be sucked through the next selection valve 52, and wherein a signal value transmitted by the second photodetector 32 upon receiving light that has passed through the comparing passage 12 from the second LED 22 is applied as a correction to a signal value transmitted by the first photodetector 31 when the sample gas is fed into the measuring passage 11, and the concentration measuring apparatus 100 measures the concentration of the chlorine dioxide gas in the enclosed space R based on the corrected signal value."

A concentration measuring apparatus 100 according to the invention described above is used as shown in FIG. 1. FIG. 1 shows part of a manufacturing plant for medicine or foods, and the concentration measuring apparatus 100 is installed in a corridor outside an enclosed space R in which actual manufacture of medicine etc. takes place.

The concentration measuring apparatus 100 selectively takes in sample gas from a plurality of locations within the enclosed space R via a conduit 50 shown in FIG. 2, and measures the concentration of chlorine dioxide gas in the sample gas. Measured specimen chlorine dioxide gas is then removed by an eliminator 54 shown in FIG. 2 and is discharged by a pump 51 into the corridor or outside, for example, via a discharge pipe 55 shown in FIG. 1.

As shown in FIG. 2, the conduit 50 supplies sample gas to the concentration measuring apparatus 100 from a plurality of locations within the enclosed space R (represented by five locations in FIG. 2) via sample gas suction tubes, due to a suction of the pump 51 provided immediately prior to the discharge pipe 55. A selection valve 52 is separately provided to each of the suction tubes. Each selection valve 52 is controlled to open and close so as to only feed sample gas to the concentration measuring apparatus 100 via any one of the five suction tubes, such that only sample gas from a selection valve 52 that is open will be sucked into the concentration measuring apparatus 100 via an open inspection valve 53.

The concentration measuring apparatus 100 is used when filling the enclosed space R with chlorine dioxide gas from a chlorine dioxide gas generator 200 shown in FIG. 2 and performing fumigation, or after the fumigation is completed. At the time of use, sample gas from the enclosed space R is fed into and made to flow through a measuring passage 11 formed in a main body 10 of the concentration measuring apparatus 100, as shown in FIG. 3. A first LED 21, second LED 22, first photodetector 31 and second photodetector 32 are operated so as to continuously measure the concentration of chlorine dioxide gas in the sample gas.

First, describing the operation of the first LED 21 provided at one side of the measuring passage 11 and the first photodetector 31 provided at the other side to receive light from the first LED 21, the first LED 21 emits ultraviolet light with a wavelength of around 360 nm (nanometers), which is most readily absorbed by chlorine dioxide gas. Light emitted from the first LED 21 proceeds through the straight measuring passage 11 toward the first photodetector 31, and as shown in JP1979-10784 and JP1998-311790, the absorption of light by the chlorine dioxide gas differs greatly depending on the amount of chlorine dioxide gas present in the measuring passage 11. The first photodetector 31 receives light and electrically converts the amount of light and transmits it as a light amount signal Pn.

At the same time, in a comparing passage 12, light emitted from the second LED 22 is received by the second photodetector 32, which electrically converts the amount of light and transmits it as a light amount signal Pm. No chlorine dioxide gas is introduced into this comparing passage 12, and the light amount signal Pm of the second LED 22 in the comparing passage 12 and the first LED 21 in the measuring passage 11 at room temperature (that is, when the first LED 21 and second LED 22 are not generating heat) shall be $P_0$. Also, the current value applied to the first LED 21 at the time $P_0$ is obtained shall be $E_0$.

The variables $P_0$, Pn, Pm, and $E_0$ mentioned above are defined as follows:

$P_0$=The light amount signal transmitted by the second photodetector 32 upon receiving light from the second LED 22 at room temperature (there is no change in the amount of light emitted, since the LED itself is not generating heat). Naturally, the amount of chlorine dioxide gas is always 0 (zero).

Pn=The light amount signal transmitted by the first photodetector 31 upon receiving light from the first LED 21 which has reached a certain temperature, in the presence of a certain concentration of chlorine dioxide gas.

Pm=The light amount signal transmitted by the second photodetector 32 upon receiving light from the second LED 22 which has reached a certain temperature (with no chlorine dioxide gas present).

$E_0$=The current value applied to the first LED 21 at the time when $P_0$ is obtained.

It should be noted that the terms "room temperature", "a certain temperature", and simply "temperature" described above and below all refer to the temperatures of the first LED 21 and the second LED 22 themselves at the time.

Moving on to describe the operation of the second LED 22 provided at one side of the comparing passage 12 and the second photodetector 32 provided at the other side to receive light from the second LED 22, the second LED 22 has the exact same properties as the aforementioned first LED 21, and emits ultraviolet light with a wavelength of around 360 nm, which is most readily absorbed by chlorine dioxide gas. The properties of the second LED 22 have been made the same as those of the first LED 21 because if the functions of the second LED 22 when the same current is applied were different from those of the first LED 21, then the second LED 22 would not be a suitable reference for comparison with the first LED 21. To put it simply, an LED with the same product number made by the same maker as the first LED 21 is used as the second LED 22.

No chlorine dioxide gas enters the comparing passage 12 in which the second LED 22 and the second photodetector 32 are installed. Instead, the comparing passage 12 is filled only with air from the location where the concentration measuring apparatus 100 is provided. As such, the second LED 22 and second photodetector 32 only perform measurements in which the light simply passes through air. However, this means that the second LED 22 and second photodetector 32 are adapted to measure changes in light emission amount due to temperature changes of the first LED 21 which has properties that are identical to those of the second LED 22.

In general, as mentioned above, when an LED emits light, the LED itself will generate heat and become warm, which changes the amount of light emitted as the temperature of the LED increases. This phenomenon will occur simultaneously and in the same manner for the first LED 21 and second LED 22 as they have identical properties, and the light amount signal Pn of the chlorine dioxide gas measured by the first photodetector 31 when the first LED 21 is at a high temperature will not represent the actual concentration of chlorine dioxide gas. The same is true regarding deterioration of the LED over time.

$P_0$ is defined as the light amount signal transmitted by the second photodetector 32 upon receiving light from the second LED 22 at room temperature, with no chlorine dioxide gas present. At room temperature and when there is no chlorine dioxide gas present in the measuring passage 11, the light amount signal Pn emitted by the first LED 21 will be $P_0$. Accordingly, $P_0$ can be redefined as follows:

$P_0$=The light amount signal transmitted by the first photodetector 31 upon receiving light emitted from the first LED 21 at room temperature when no chlorine dioxide gas is present in the measuring passage 11.

Thus, it is possible to utilize the following relationship:

$P_0$=The light amount signal transmitted by the second photodetector 32 upon receiving light from the second LED 22 at room temperature (there is no change in the amount of light emitted, since the LED itself is not generating heat). Naturally, the amount of chlorine dioxide gas is always 0 (zero), equals:

The light amount signal transmitted by the first photodetector 31 upon receiving light emitted from the first LED 21 at room temperature when no chlorine dioxide gas is present in the measuring passage 11.

By letting X be a portion of light amount that is reduced due to a temperature change of the second LED 22 to a certain temperature;

and letting Y be a portion of light amount of the light amount signal transmitted by the first photodetector 31, which is reduced simply due to the presence of chlorine dioxide gas, then the following relationships and equations are realized:

Regarding the Second Photodetector 32:

Since Pm measures the decrement X from $P_0$ due to a change in temperature of the second LED 22, $$Pm = P_0 - X$$

accordingly, $$X = P_0 - Pm$$

Regarding the First Photodetector 31:

Since Pn measures the decrement from $P_0$ due to a change in temperature of the first LED 21 (=X) and the decrement Y due to the presence of chlorine dioxide gas, $$Pn = P_0 - (X + Y)$$
$$= P_0 - (P_0 - Pm + Y)$$

accordingly, $$Y = Pn - Pm$$

As described above, the concentration measuring apparatus 100 obtains the variables $P_0$, $E_0$, Pn, and Pm, and the values of these variables allow for calculation of a light amount signal P to be indicated by the first photodetector 31 when chlorine dioxide gas is present in the enclosed space R at a certain temperature, after temperature correction of the first LED 21 (and subsequently the second LED 22), and a concentration D of the chlorine dioxide gas in the enclosed space R, using the following first and second calculation methods. The first and second calculation methods are based on the thought processes described below.

(Thought Process and Concentration Calculation According to the First Calculation Method)

When chlorine dioxide gas is present in the enclosed space R at a certain temperature, it is fed as a sample gas into the measuring passage 11 and measured, whereby Pn is obtained by the first photodetector 31. Pn thus obtained includes a change in light amount due to a temperature change of the first LED 21 (and subsequently the second LED 22). This change in light amount of the first LED 21 corresponds to a tare weight when measuring, for example, a person's body weight with their clothes still on, and since the "tare weight" in this case is obtained in the comparing passage 12 as Pm, it is possible to simply use the value of Pm to correct the value of Pn.

Based on the above thought process, the light amount signal P to be indicated by the first photodetector 31 when chlorine dioxide gas is present in the enclosed space R at a certain temperature, after temperature correction of the first LED 21 (and subsequently the second LED 22) is:

$P = Y =$ a portion of light amount of the light amount signal transmitted by the first photodetector 31, which is reduced simply due to the presence of chlorine dioxide gas $= Pn - Pm$ As such, this constitutes data from which the actual concentration of the chlorine dioxide gas present in the enclosed space R can be calculated. In other words, the concentration D of the chlorine dioxide gas present in the enclosed space R at a certain temperature is:

$$D = k_1 * (Pn - Pm),$$

wherein $k_1$=concentration conversion constant.

(Thought Process and Concentration Calculation According to the Second Calculation Method)

It is known that when the voltage applied to the first LED 21 and the second LED 22 is the same in a case where the LEDs are at room temperature as in a case where they have become warmer than room temperature, the light emission amounts of the first and second LEDs will decrease in the latter case. It is also known that by proportionally increasing the applied voltage, the light emission amounts of the first LED 21 and the second LED 22 can be increased. In other words, the decrease in light emission amount of the first LED 21 and the second LED 22 due to an increase in temperature can be corrected for by increasing the applied voltage, to keep the decrease at 0, meaning that one simply has to adjust the applied voltage in response to the change in temperature of the first LED 21 and the second LED 22. This thought process is applied in the embodiment of the invention shown in FIG. 5.

As previously mentioned, the variables are defined in the following manner:

$P_0$=The light amount signal transmitted by the second photodetector 32 upon receiving light from the second LED 22 at room temperature.

Pn=The light amount signal transmitted by the first photodetector 31 upon receiving light from the first LED 21 which has reached a certain temperature, in the presence of a certain concentration of chlorine dioxide gas.

Pm=The light amount signal transmitted by the second photodetector 32 upon receiving light from the second LED 22 which has reached a certain temperature.

Since the variables are defined in this way, the voltage E to be applied in response to a change in temperature of the first LED 21 and the second LED 22 is:

$$E = E_0 * (P_0/Pm).$$

As a result of the above, if the voltage E is applied in response to a change in temperature in the first LED 21 and the second LED 22, the signal Pn can be used as data indicating the actual concentration D of the chlorine dioxide gas, wherein:

$$D = k2 * Pm,$$

wherein k2=concentration conversion constant.

As described above, the concentration measuring apparatus according to claim 1 has in its main body 10 a comparing passage 12 formed separately from a measuring passage 11, the comparing passage 12 provided with a second LED 22 and a second photodetector 32, which enables calculation of Pm and E, which are essential for respectively the first calculation method and the second calculation method, allowing for both the first and second calculation methods to be employed. By contrast, the techniques disclosed in JP1979-10784 and JP1998-311790 only measure the Pn described above.

Accordingly, the concentration measuring apparatus 100 according to claim 1 is capable of continuously and precisely measuring chlorine dioxide gas concentration by making a correction for a change in light emission rate of the LED due to heating and passage of time, and constantly applying the correction to the optical absorption rate of the chlorine dioxide gas at the photodetector.

In order to solve the aforementioned problem, the invention according to claim 2 employs the following means, in addition to the concentration measuring apparatus 100 according to claim 1:

"The first LED 21 and the second LED 22 are integrated in a pedestal 23 made of a material with good heat conductivity"

The present invention was originally conceived based on the recognition that the light emission rates of the first LED 21 and second LED 22 change due to self-heating, and is characterized by applying a correction in response to the temperature change to the data used for determining the concentration of the chlorine dioxide gas. For the sake of comparison, the invention utilizes a first LED 21 and a second LED 22 which have identical properties, and the changes in temperature of these first and second LEDs must not be influenced by ambient conditions.

In other words, the first LED 21 and the second LED 22 should have identical properties, and if either of them were to heat up or cool down quicker due to thermal conduction, or if the rate of heating or cooling differed from that of the other, it would not be a suitable reference for comparison with the other LED.

Thus, in the concentration measuring apparatus 100 according to claim 2, in order to further ensure that the heating properties of the first LED 21 and the second LED 22 are identical, the first LED 21 and second LED 22 are integrated in a pedestal 23 made of a good heat conductive material, as shown in FIG. 3a. In an embodiment described below the pedestal 23 is a block made of aluminum. This arrangement allows the first LED 21 and the second LED 22 to be suitable for comparison with one another in terms of heat conditions, either at room temperature or when self-heated due to operation.

Accordingly, the concentration measuring apparatus 100 according to claim 2, while obviously exhibiting the same functions as the apparatus according to claim 1, constantly keeps the temperature conditions of the first LED 21 and the second LED 22 by means of the pedestal 23.

In order to solve the aforementioned problem, the invention according to claim 3 employs the following means, in addition to the concentration measuring apparatus 100 according to either one of claim 1 or 2:

"Moisture condensed on the transparent bodies 13 can be removed by means of heaters 40 provided in the vicinity of the transparent bodies 13."

Generally, chlorine dioxide is produced as an aqueous solution, and is separated from this solution when used as a gas for fumigation. As explained above, the chlorine dioxide gas separated from the solution will inevitably contain moisture, which causes condensation.

Meanwhile, measuring the concentration of chlorine dioxide gas, which can cause harm to the human body, using light in the range near ultraviolet, requires that transparent bodies 13 be provided on both sides of a measuring passage 11 formed in a main body 10, into which chlorine dioxide gas is fed, and that a first LED 21 and a first photodetector 31 be arranged on the outside of these transparent bodies 13. If the sample gas fed into the measuring passage 11 contains moisture, condensation may occur on the inner surfaces of the transparent bodies 13 while the concentration measuring apparatus 100 is measuring. In light of the conditions for producing chlorine dioxide gas as mentioned above, it is very likely that condensation will occur.

The easiest way of preventing condensation on the inner surfaces of the transparent bodies 13 is to pre-heat the measuring passage 11 and/or the transparent bodies, making condensation less likely to occur. To that end, the concentration measuring apparatus according to claim 3 includes heaters 40 provided in the vicinity of the transparent bodies 13, allowing for removal of moisture that has condensed on the transparent bodies 13.

Accordingly, the concentration measuring apparatus 100 according to claim 3, while exhibiting the same functions as the apparatus according to claim 1 or 2, is capable of preventing condensation from occurring even if the sample gas contains moisture, and is capable of continuously and precisely measuring chlorine dioxide gas concentration.

Effects of the Invention

As described above, the features of the present invention are:

"A concentration measuring apparatus for measuring a concentration of chlorine dioxide gas in a sample gas selectively fed into the apparatus from a plurality of locations in an enclosed space via a conduit, by means of a change in an amount of ultraviolet light from a LED, using the sample gas which is separately sucked through a plurality of sample gas suction tubes in the enclosed space and fresh air which is sucked from outside the enclosed space, the apparatus comprising:

a main body having a measuring passage surrounded by a pair of transparent bodies that transmit light and into which the sample gas or the fresh air is fed respectively from inside or outside of the enclosed space and then discharged, and a comparing passage arranged in the vicinity of the measuring passage and into which only fresh air is fed from outside the enclosed space;

a first LED and a second LED for emitting ultraviolet light which both have identical properties and are mounted at one end of the measuring passage and at one end of the comparing passage, respectively;

a first photodetector and a second photodetector for receiving light respectively from the first LED and the second LED and detecting a light emission amount thereof;

a plurality of selection valves for individual selection of the sample gas suction tubes;

an inspection valve for controlling feeding of the sample gas from the suction tubes into the main body;

an air valve configured to open to enable suction of fresh air from outside the enclosed space when all of the selection valves are closed; and a pump for enabling suction of the sample gas or fresh air into the main body when either the air valve or any of the selection valves are open, wherein when selectively sucking sample gas from inside the enclosed space due to the suction of the pump and the selective action of the selection valves over a predetermined time, the inspection valve and the selection valve are temporarily closed and the air valve is opened, so that fresh air is sucked into the main body to discharge all of the sample gas that has been examined, after which the air valve is closed and the inspection valve and another selection valve are opened so that sample gas can be sucked through the next selection valve, and wherein a signal value transmitted by the second photodetector upon receiving light that has passed through the comparing passage from the second LED is applied as a correction to a signal value transmitted by the first photodetector when the sample gas is fed into the measuring passage, and the concentration measuring apparatus measures the concentration of the chlorine dioxide gas in the enclosed space based on the corrected signal value."

These features make it possible to provide a concentration measuring apparatus 100 that is capable of continuously and precisely measuring chlorine dioxide gas concentration by making a correction for a change in light emission rate of the LED due to heating and passage of time, and constantly applying the correction to the optical absorption rate of the chlorine dioxide gas at the photodetector.

More specifically, in the chlorine dioxide gas concentration measuring apparatus 100 according to claim 1, the sample gas from the enclosed space R or fresh air from outside is discharged after being supplied to the measuring passage 11 in the main body 10. That is to say, once measuring of chlorine dioxide gas concentration in a sample gas sucked from one location in the enclosed space R is finished, all of the sample gas is discharged by sucking fresh air into the measuring passage 11 of the main body 10, and then sample gas from another location in the enclosed space R is sucked into the measuring passage 11 for concentration measuring. Therefore, even if the enclosed space R is very large, it is possible to measure the concentration of chlorine dioxide gas at any location within the enclosed space R in a short time, continuously, and in real-time. In other words, the concentration measuring apparatus 100 according to claim 1 is capable of solving the problem "(5) In actual fumigation disinfection using chlorine dioxide gas, with existing LEDs and photodetectors having an error range of 2% to 3%, concentration of the gas must be controlled under very strict conditions; concentration levels must be kept low at 300 ppm, and the process takes about 5 to 6 hours" discussed above in "The Problem to be Solved by the Invention."

In addition, with the concentration measuring apparatus 100 including "heaters 40 provided in the vicinity of the transparent bodies 13, allowing for removal of moisture that has condensed on the transparent bodies 13," the concentration measuring apparatus 100 will be capable of preventing condensation from occurring even if the sample gas contains moisture, and continuously and precisely measuring chlorine dioxide gas concentration.

BRIEF DESCRIPTION OF THE DRAWINGS

FIG. 6 shows the technical matter of JP1979-10784, wherein FIG. 6a is a side view, and FIG. 6b is a cross-sectional view.

DETAILED DESCRIPTION OF THE INVENTION

Figure 1:
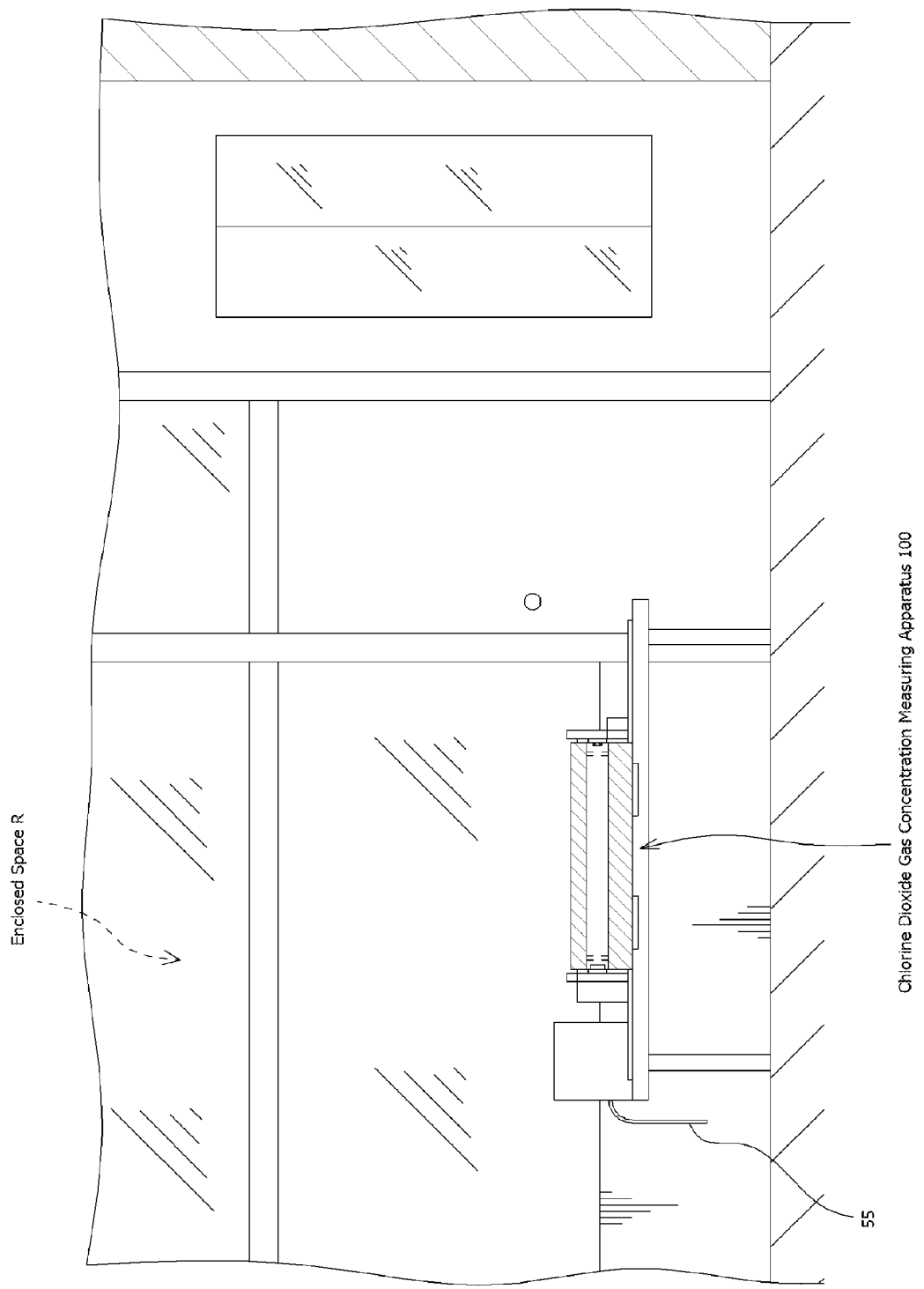
FIG. 1 is a partial cross-section view of the concentration measuring apparatus 100 according to the present invention in use.

Next, describing the invention according to the aforementioned claims in terms of the concentration measuring apparatus 100 according to the embodiments shown in the drawings, FIG. 1 shows the concentration apparatus 100 according to an embodiment of the invention being used for detecting the concentration of chlorine dioxide gas in an actual enclosed space R. FIG. 1 shows part of the interior of a manufacturing plant for medicine or food, with the concentration measuring apparatus 100 being installed in a corridor outside of the enclosed space R in which actual manufacture takes place. The concentration measuring apparatus 100 selectively takes in sample gas from a plurality of locations within the enclosed space R via a conduit 50 shown in FIG. 2, and measures the concentration of chlorine dioxide gas in the sample gas. Measured specimen chlorine dioxide gas is then removed by an eliminator 54 shown in FIG. 2 and is discharged by a pump 51 into the corridor or outside, for example, via a discharge pipe 55 shown in FIG. 1.

Figure 2:
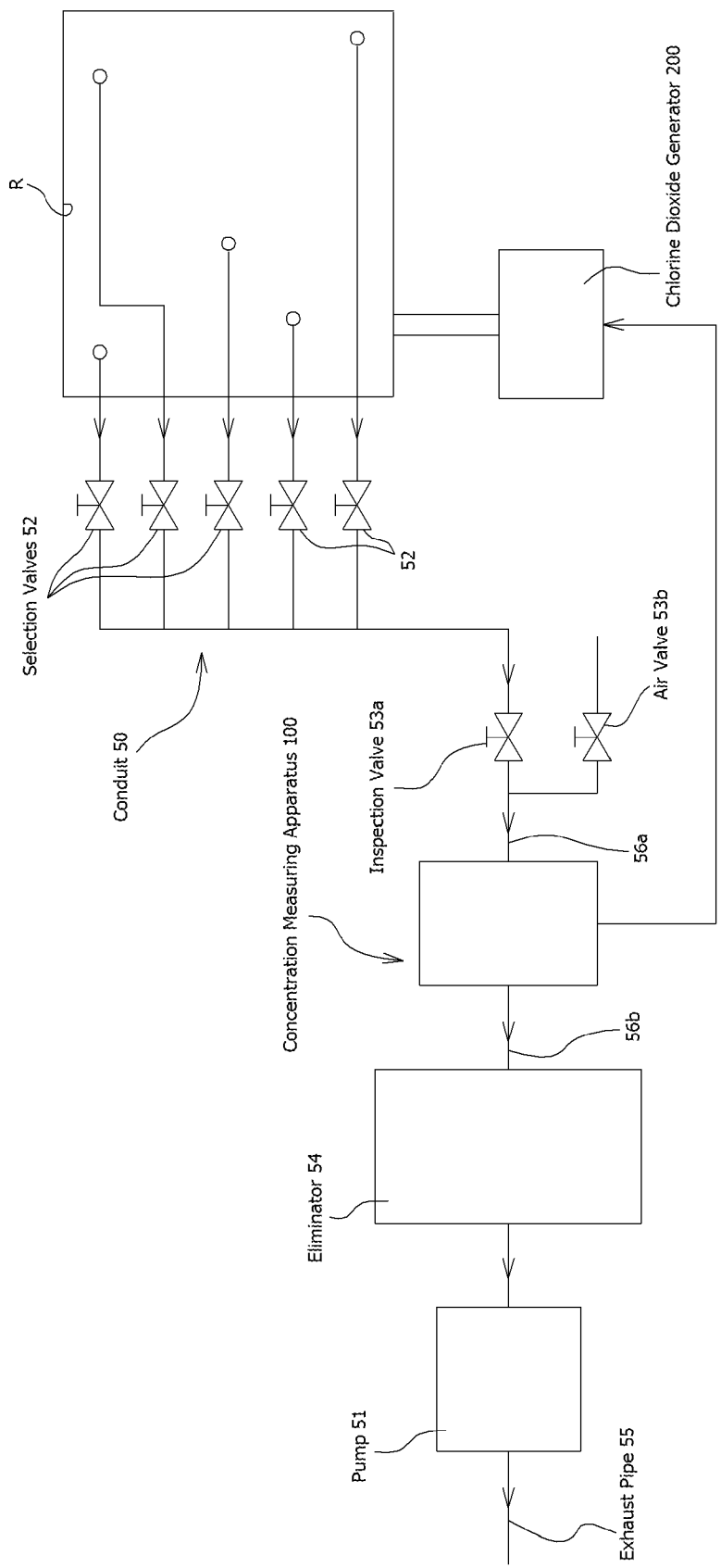
FIG. 2 is a circuit diagram schematically showing the relationship between the concentration measuring apparatus 100 and peripheral equipment such as the conduit 50 and the pump 51.

As shown in FIG. 2, the conduit 50 supplies sample gas to the concentration measuring apparatus 100 from a plurality of locations within the enclosed space R (represented by five locations in FIG. 2) via sample gas suction tubes, due to a suction of the pump 51 provided immediately prior to the discharge pipe 55. A selection valve 52 is separately provided to each of the suction tubes. Each selection valve 52 is controlled to open and close so as to only feed sample gas to the concentration measuring apparatus 100 via any one of the five suction tubes, such that only sample gas from a selection valve 52 that is open will be sucked into the concentration measuring apparatus 100 via an open inspection valve 53a.

When detecting the concentration of chlorine dioxide gas in the enclosed space R over a predetermined time, the concentration measuring apparatus 100 according to this embodiment is further configured to temporarily close the inspection valve 53a and the selection valves 52, and open the air valve 53b shown in FIG. 2 to take in outside air which does not contain any chlorine dioxide gas so as to discharge all of the previously examined sample gas that remains in the concentration measuring apparatus 100. When all of the sample gas has been discharged, the concentration measuring apparatus 100 closes the air valve 53b and opens the inspection valve 53a and a selected selection valve 52 to feed new sample gas into the concentration measuring apparatus 100 and carry out the next required concentration measurement.

As described above, the concentration measuring apparatus 100 according to the present embodiment takes in sample gas from multiple locations within the enclosed space R into the concentration measuring apparatus 100 due to a suction of the pump 51 provided immediately prior to the discharge pipe 55. As shown in FIG. 2, an eliminator 54 for removing chlorine dioxide gas from the sucked gas is provided upstream of the pump 51. The eliminator 54 contains active carbon which adsorbs chlorine dioxide gas, which prevents chlorine dioxide gas from directly entering the pump 51 and possibly damaging its components, and also ensures that no chlorine dioxide gas remains in the gas discharged from the discharge pipe 55.

As shown in FIG. 2, the concentration measuring apparatus 100 according to the present embodiment is also configured to control a chlorine dioxide gas generator 200 for supplying produced chlorine dioxide gas to the enclosed space R. Thus, if the concentration measuring apparatus 100 detects a chlorine dioxide concentration lower than the 300 ppm required for fumigation, the concentration measuring apparatus 100 performs electrical control to operate the chlorine dioxide gas generator 200, allowing it to feed produced chlorine dioxide gas into the enclosed space R. This chlorine dioxide gas generator 200 can for example be the gas generator proposed by the applicant in Japanese Patent No. 5,639,294.

The concentration measuring apparatus 100 may be used when disinfecting an enclosed space R using a feeder (not shown) to feed chlorine dioxide gas into the enclosed space R, or after disinfection is finished. As shown in FIG. 3, sample gas is fed into and made to flow through a measuring passage 11 formed in a main body 10 of the concentration measuring apparatus 100.

Figure 3A:
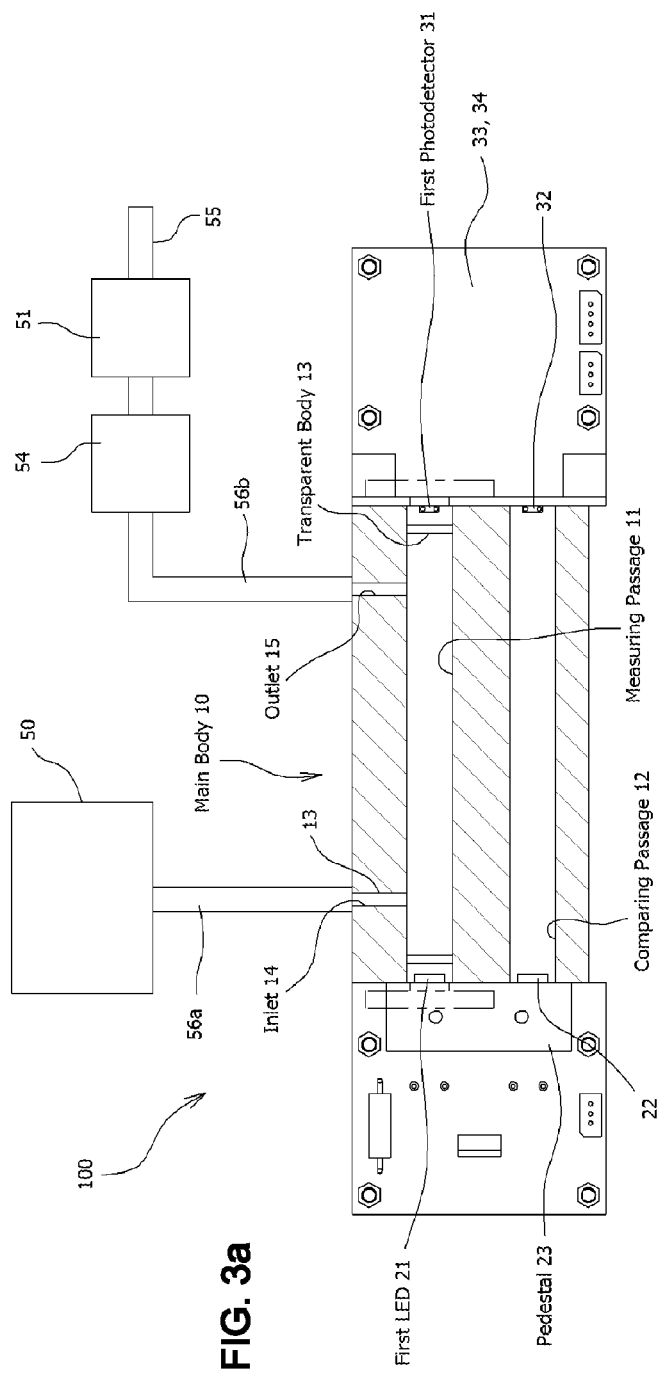
FIG. 3a is a partial cross-sectional view of the concentration measuring apparatus 100.
Figure 3B:
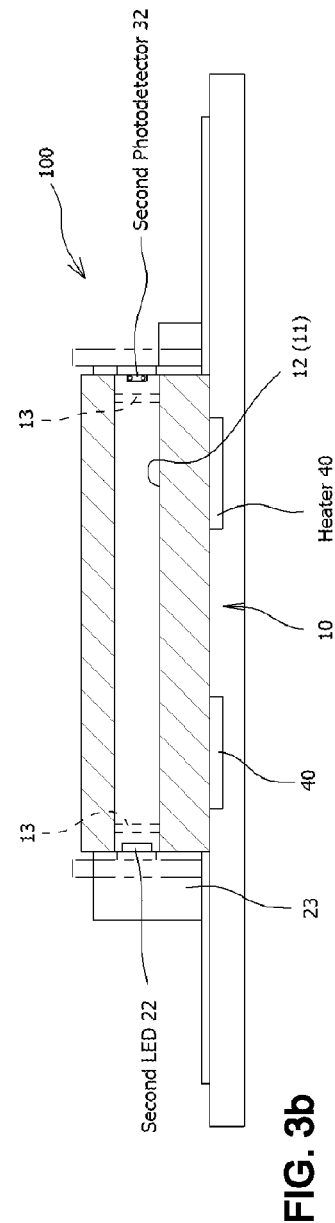
FIG. 3b is a front view of the concentration measuring apparatus 100.
Figure 4:
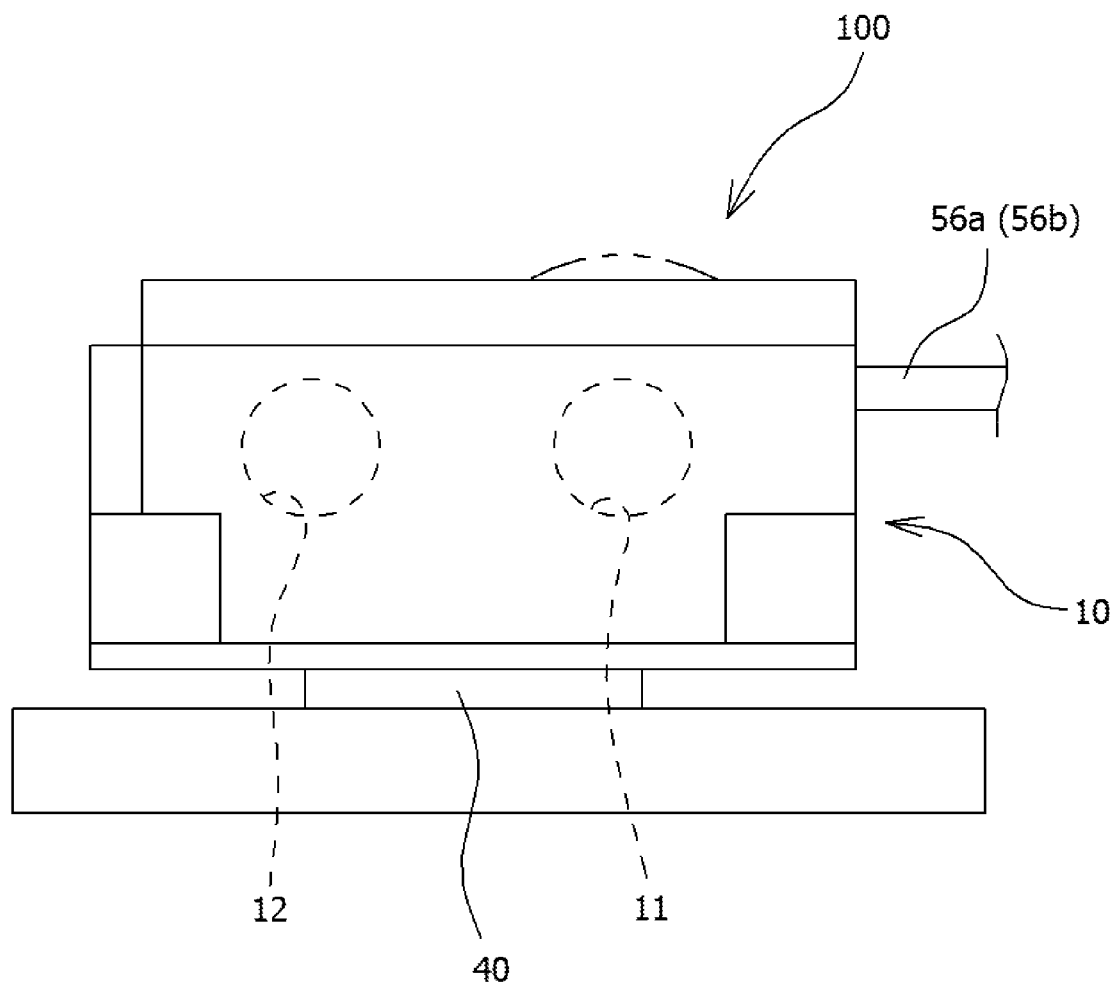
FIG. 4 is an enlarged side view of the concentration measuring apparatus 100.
Figure 5:
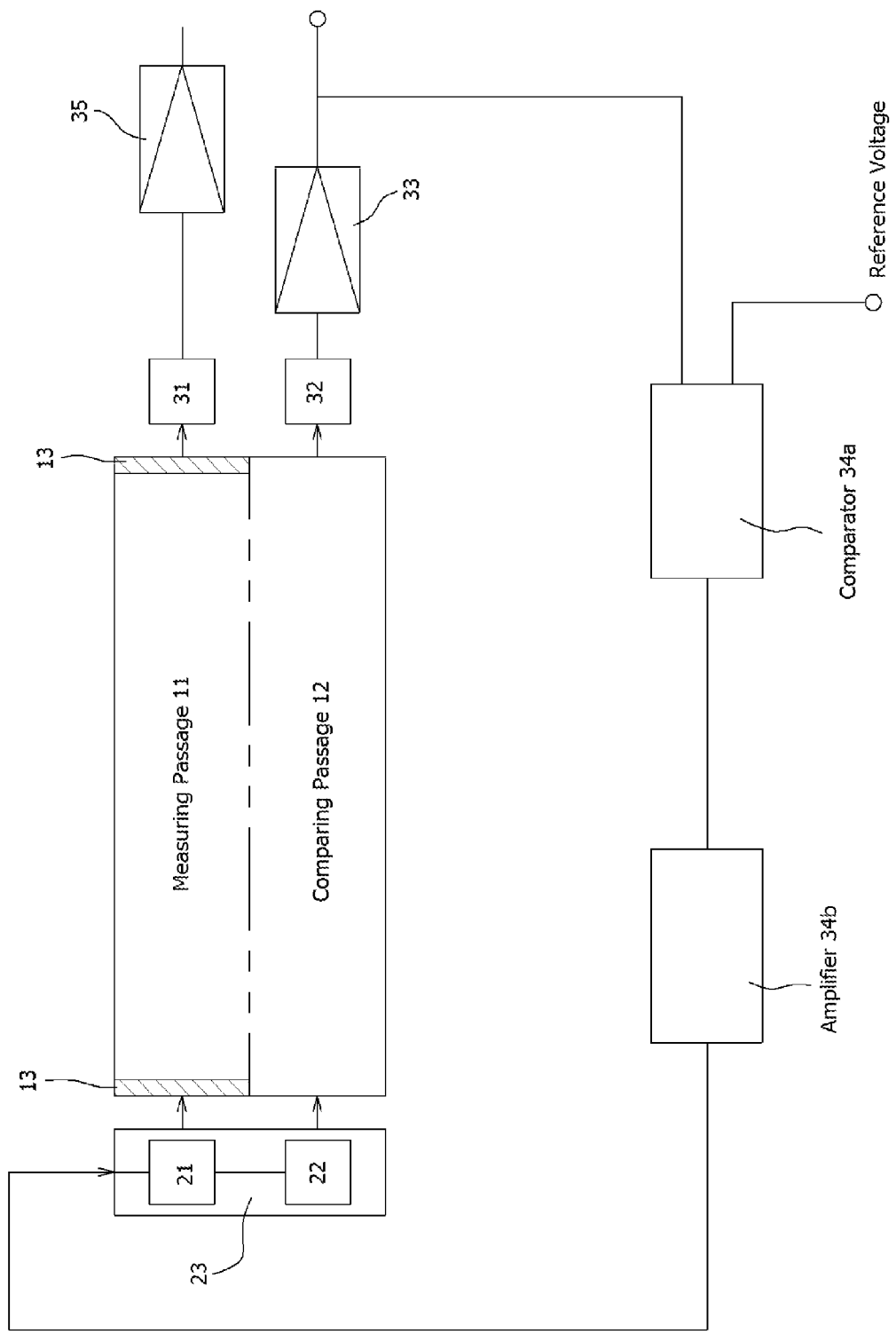
FIG. 5 is an electrical circuit diagram schematically showing an embodiment of the concentration measuring apparatus 100.
Figure 6:
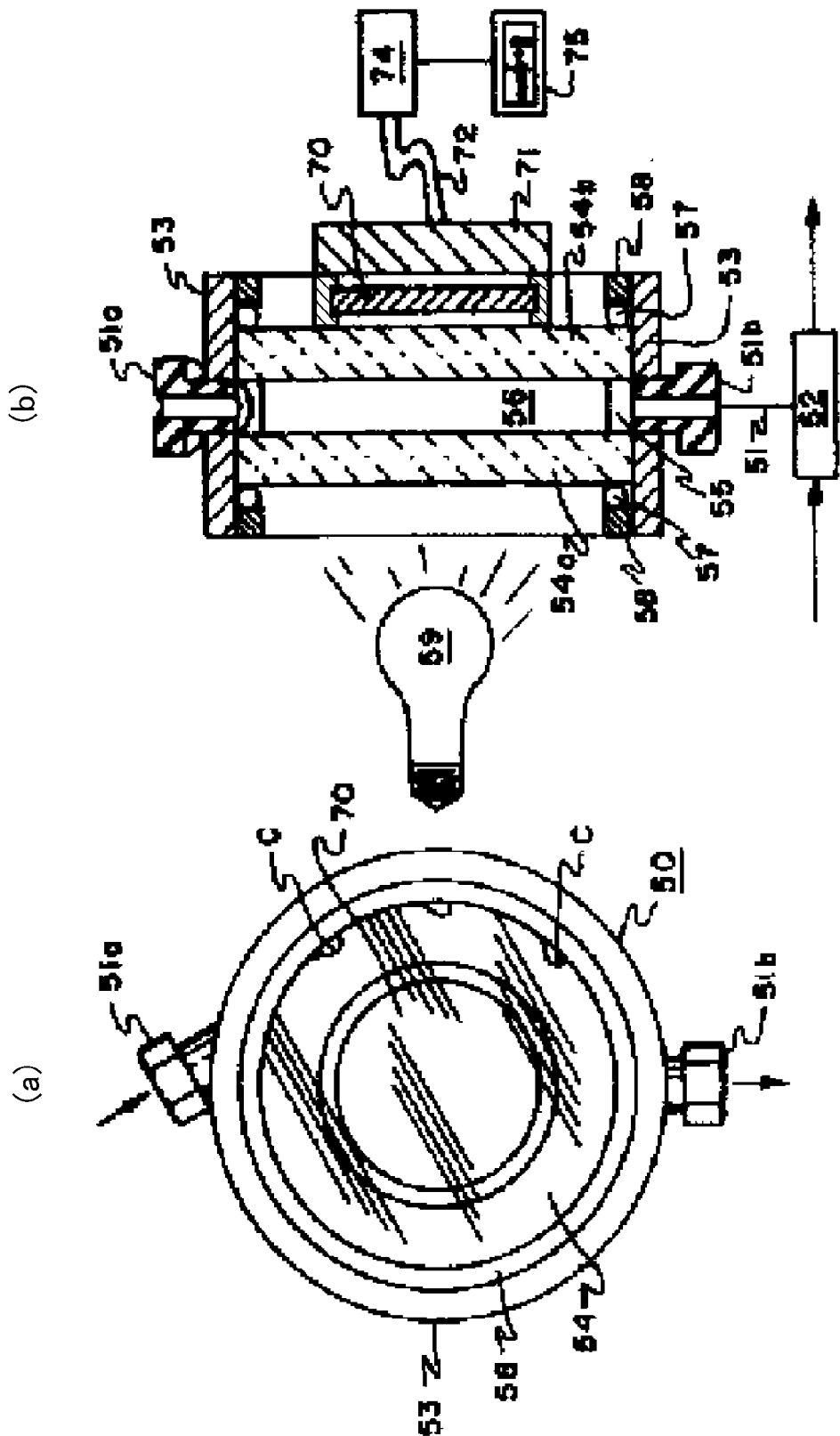
Figure 7:
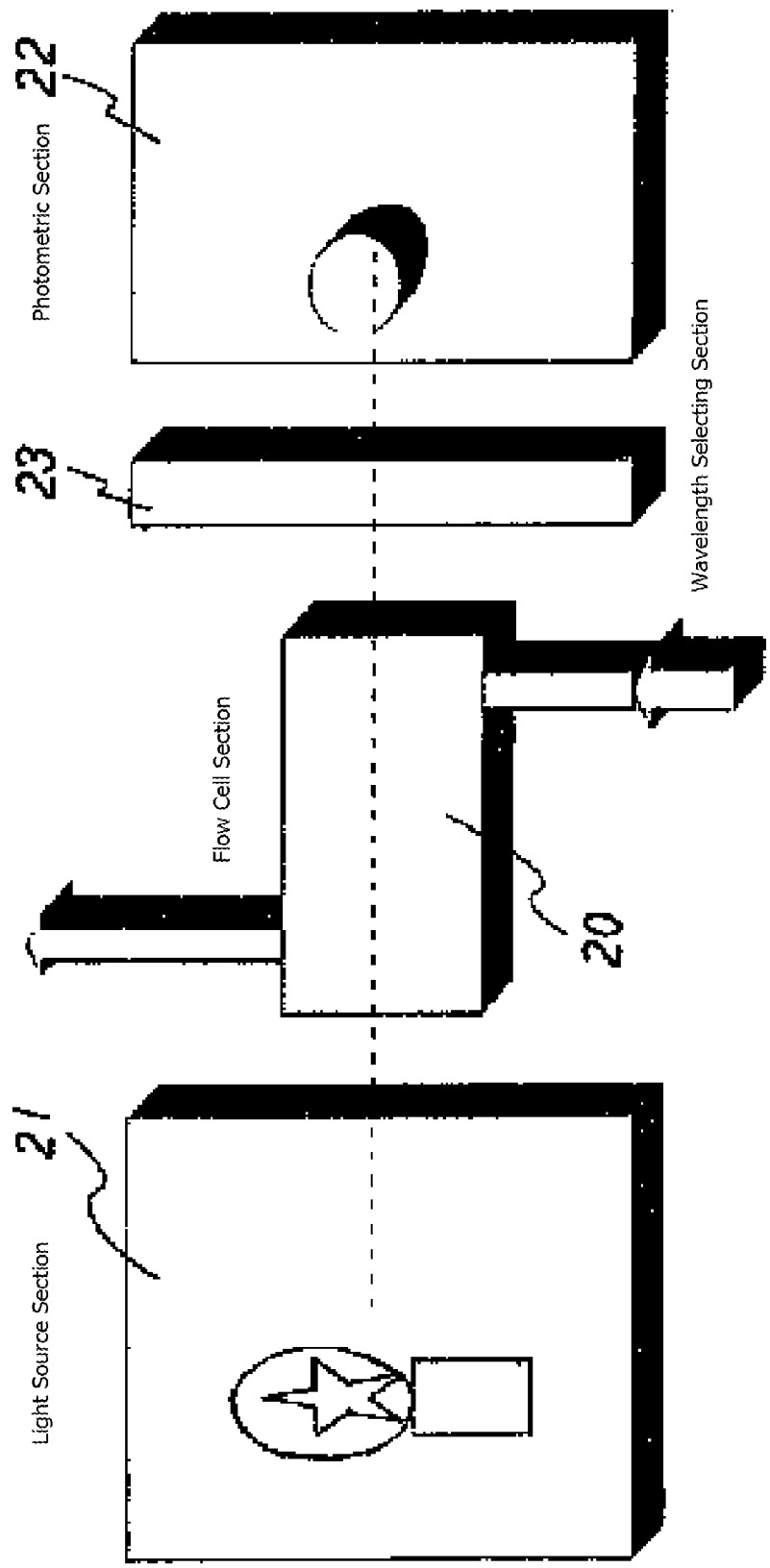
FIG. 7 is a plan view of a schematic arrangement of the technical matter of JP JP 1998-311790.

As shown in FIGS. 3 and 4, the concentration measuring apparatus 100 according to the present embodiment has a main body which has a measuring passage 11 that is surrounded by a pair of transparent bodies 13 which transmit light, into which specimen gas or fresh air is fed respectively from the inside or outside of the enclosed space R and then discharged, and a comparing passage 12 arranged in the vicinity of the measuring passage 11, into which no specimen gas from the enclosed space R is fed. In addition, at a part of the main body 10, there are formed an inlet 14 for taking in specimen gas containing chlorine dioxide gas from within the enclosed space R or fresh air from the outside corridor, and an outlet 15 for discharging these gases mainly into the enclosed space R. The inlet 14 and the outlet 15 are respectively connected to a feed pipe 56a and a discharge pipe 56b. As previously mentioned, a suction hose for taking in air from the outside corridor into the concentration measuring apparatus 100 protrudes out into the corridor via an air valve 53b.

Further, as shown in FIG. 3a, in the concentration measuring apparatus 100, a first LED 21 and a second LED 22 which both have identical properties and emit ultraviolet light are mounted at one end of the measuring passage 11 and one end of the comparing passage 12, respectively. Mounted at the respective other end of the measuring passage 11 and the comparing passage 12 are a first photodetector 31 and a second photodetector 32 which receive light respectively from the first LED 21 and the second LED 22 and detect the light emission amount thereof. By passing a current through the first LED 21 and the second LED 22, they emit light with a wavelength in the ultraviolet region, specifically with a wavelength around 360 nm.

In the concentration measuring apparatus 100 according to the present embodiment, the first LED 21 and second LED 22 are mounted to a pedestal 23, specifically an aluminum block. This pedestal 23 is formed of a material with good thermal conductivity, allowing it to support the first LED 21 and second LED 22 on the main body 10 while maintaining identical temperature conditions of the first LED 21 and the second LED 22.

The first photodetector 31 and second photodetector 32 which detect the amount of light emitted by the first LED 21 and second LED 22 each convert the received amount of light into an electrical signal. In the present embodiment, the aforementioned second calculation method is employed. Therefore, light amount signals from amplifiers 35, 33 connected to the first photodetector 31 and second photodetector 32 are used for the following calculations:

$P_0$=The light amount signal transmitted by the second photodetector 32 upon receiving light from the second LED 22 at room temperature.

$E_0$=The current value applied to the first LED 21 at the time when $P_0$ is obtained.

$Pm$=The light amount signal transmitted by the second photodetector 32 upon receiving light from the second LED 22 which has reached a certain temperature.

As such, the voltage E to be applied in response to the change in temperature of the first LED 21 and second LED 22 is calculated at a comparator 34a and amplifier 34b as follows:

$$E=E_0*(P_0/Pm)$$

This current E is then applied to the first LED 21 at the measuring passage 11.

In addition, as shown in FIG. 4, the concentration measuring apparatus 100 according to the present embodiment has a heater 40 mounted to a portion of the main body 10 adjacent the entire length of the measuring passage 11. This heater 40 prevents condensation to occur on the transparent bodies 13.

DESCRIPTION OF THE REFERENCE NUMERALS

100 Concentration measuring apparatus
10 Main body
11 Measuring passage
12 Comparing passage
13 Transparent body
14 Inlet
15 Outlet
21 First LED
22 Second LED
23 Pedestal
31 First photodetector
32 Second photodetector
33, 35 Amplifier
34a Comparator
34b Amplifier
40 Heater
50 Conduit
51 Pump
52 Selection valve
53a Inspection valve
53b Air valve
54 Eliminator
55 Discharge pipe
56a Feed pipe
56b Discharge pipe
R Enclosed space
200 (Chlorine dioxide gas) generator

What is claimed is:

1. A concentration measuring apparatus for measuring a concentration of chlorine dioxide gas in a sample gas selectively fed via a conduit into the apparatus from a plurality of locations in an enclosed space, by means of a change in an amount of ultraviolet light from a LED, using the sample gas which is separately sucked through a plurality of sample gas suction tubes in the enclosed space and fresh air which is sucked from outside the enclosed space, the apparatus comprising:

a main body having a measuring passage surrounded by a pair of transparent walls into which the sample gas or fresh air is fed respectively from inside or outside of the enclosed space and then discharged, and a comparing passage arranged in the vicinity of the measuring passage and into which only fresh air is fed from outside the enclosed space;

a first LED and a second LED for emitting ultraviolet light which both have identical properties and are respectively mounted at one end of the measuring passage and at one end of the comparing passage;

a first photodetector and a second photodetector for receiving light respectively from the first LED and the second LED and detecting a light emission amount thereof;

a plurality of selection valves for individual selection of the sample gas suction tubes;

a single inspection valve disposed upstream of the main body for controlling feeding of the sample gas from the suction tubes into the main body;

an air valve disposed upstream of the main body, the air valve configured to open to enable suction of fresh air from outside the enclosed space when all of the selection valves are closed wherein the air valve and the inspection valve are connected in parallel fluid communication with the main body; and a pump disposed downstream of the main body for enabling suction of the sample gas or fresh air into the main body when either the air valve or any of the selection valves are open, wherein after selectively sucking sample gas from inside the enclosed space due to the suction of the pump and the selective action of the selection valves over a predetermined time, the inspection valve and the selection valve are temporarily closed and the air valve is opened, so that fresh air is sucked into the main body so as to discharge all of the sample gas that has been examined, after which the air valve is closed and the inspection valve and another selection valve are opened so that sample gas is sucked through the next selection valve, and wherein a signal value transmitted by the second photodetector upon receiving light that has passed through the comparing passage from the second LED is applied as a correction to a signal value transmitted by the first photodetector when the sample gas is fed into the measuring passage, and the concentration measuring apparatus measures the concentration of the chlorine dioxide gas in the enclosed space based on the corrected signal value.

2. The concentration measuring apparatus according to claim 1, wherein the first LED and the second LED are integrated in a pedestal made of a material with good heat conductivity.

3. The concentration measuring apparatus according to claim 1, wherein moisture condensed on the transparent walls can be removed by means of heaters provided in the vicinity of the transparent walls.

4. The concentration measuring apparatus according to claim 2, wherein moisture condensed on the transparent walls can be removed by means of heaters provided in the vicinity of the transparent bodies.

* * * * *